United States Patent

US005847229A

Bigorra Llosas et al.

[11] Patent Number: 5,847,229
[45] Date of Patent: Dec. 8, 1998

[54] PROCESS FOR THE PRODUCTION OF END-CAPPED NONIONIC SURFACTANTS

[75] Inventors: Joaquim Bigorra Llosas, Sabadell; Nuria Bonastre, Barberà del Vallès; Antonio Trius Oliva, Valldoreix; Rafael Pi Subirana, Granollers, all of Spain

[73] Assignee: Henkel Kommanditgesellschaft auf Aktien, Duesseldorf, Germany

[21] Appl. No.: 836,110

[22] PCT Filed: Oct. 24, 1995

[86] PCT No.: PCT/EP95/04156

§ 371 Date: Jun. 9, 1997

§ 102(e) Date: Jun. 9, 1997

[87] PCT Pub. No.: WO96/14377

PCT Pub. Date: May 17, 1996

[30] Foreign Application Priority Data

Nov. 2, 1994 [DE] Germany .............. P 44 39 086.6

[51] Int. Cl.$^6$ ................................................ C07C 43/11
[52] U.S. Cl. ............................................................ 568/619
[58] Field of Search ............................................... 568/619

[56] References Cited

U.S. PATENT DOCUMENTS

| 4,548,729 | 10/1985 | Schmid et al. ................ 252/174.21 |
| 4,587,365 | 5/1986 | Anchor ................................. 568/619 |
| 4,624,803 | 11/1986 | Balzer et al. ......................... 252/527 |
| 4,922,029 | 5/1990 | Birnbach et al. ..................... 568/616 |
| 4,942,049 | 7/1990 | Schmid et al. ........................ 426/329 |
| 4,973,423 | 11/1990 | Geke et al. ...................... 252/174.21 |
| 5,484,553 | 1/1996 | Guth, et al. .......................... 252/351 |

FOREIGN PATENT DOCUMENTS

| 1 338 277 | 4/1996 | Canada . |
| 0 124 815 | 11/1984 | European Pat. Off. . |
| 0 161 537 | 11/1985 | European Pat. Off. . |
| 0 302 487 | 2/1989 | European Pat. Off. . |
| 0 303 928 | 2/1989 | European Pat. Off. . |
| 0 324 340 | 7/1989 | European Pat. Off. . |
| 0 420 802 | 4/1991 | European Pat. Off. . |
| 0 427 088 | 5/1991 | European Pat. Off. . |
| 37 44 525 | 12/1988 | Germany . |
| 39 28 600 | 9/1991 | Germany . |
| 42 43 643 | 8/1993 | Germany . |
| 6 916 304 | 5/1970 | Netherlands . |

OTHER PUBLICATIONS

Fat. Sci. Technol., 89 (1987) p. 106.

*Primary Examiner*—Michael L. Shippen
*Attorney, Agent, or Firm*—Ernest G. Szoke; Wayne C. Jaeschke; Henry E. Millson, Jr.

[57] ABSTRACT

Process for the production of end-capped nonionic surfactants by forming an alcoholate between a fatty alcohol polyglycol ether and a solid base, reacting the alcoholate with a dialkyl sulfate, adding water to initiate phase separation, and separating the organic layer from the aqueous layer.

20 Claims, No Drawings

PROCESS FOR THE PRODUCTION OF END-CAPPED NONIONIC SURFACTANTS

BACKGROUND OF THE INVENTION

1. Field of the Invention

This invention relates to a process for the production of end-capped nonionic surfactants by forming an alcoholate between a fatty alcohol polyglycol ether and a solid base, reacting the alcoholate with a dialkyl sulfate and adding water to initiate phase separation.

2. Statement of Related Art

For a number of industrial processes, the presence of foam is extremely undesirable. For example, both in the machine washing of beer or milk bottles and in the spray cleaning of automobile panels, not only is the cleaning or degreasing effect of the surface-active formulations used an important factor, the avoidance of foam which can seriously interfere with the operation of machinery is of equal importance. This is all more the so inasmuch as, in many cases, highly active but also high-foaming anionic surfactants are used.

The problem of controlling foam has been known for some time and, accordingly, various more or less convincing solutions to the problem are known from the prior art and may be divided into two groups.

The first group comprises processes involving the addition of defoamers which are often paraffinic hydrocarbons or silicone compounds. For the described applications, however, this is mostly undesirable. The second group of processes involve the use of surface-active formulations which are themselves low-foaming and which may additionally exhibit defoaming properties. The surfactants used are generally nonionic surfactants or surfactant-like systems such as, for example, fatty alcohol propylene glycol ethers or block polymers of ethylene and propylene glycol which, unfortunately, are not sufficiently biodegradable.

End-capped fatty alcohol polyglycol ethers, so-called "mixed ethers", which are described for example by R. Piorr in Fat. Sci. Technol. 89, 106 (1987), have established themselves on the market as particularly effective low-foaming surfactants. These products are generally butyl-end-capped nonionic surfactants which are known, for example, from EP-A 0 124 815, EP-B 0 303 928, EP-B 0 324 340, EP-A 0 420 802, DE-A 3 928 600 and DE-C 4 243 643.

Methyl mixed ethers occupy a special position. They are end-capped by methyl groups and are normally obtained by reaction of the corresponding fatty alcohol polyglycol ethers with methyl halides [U.S. Pat. No. 4,587,365, BASF] or dimethyl sulfate.

In this connection, a one-pot process for the production of end-capped nonionic surfactants is known from EP 0 302 487 B1 (BASF). In this process, fatty alcohol polyglycol ethers are reacted with dialkyl sulfates in the presence of aqueous alkali metal hydroxides, the reaction taking place at a temperature in the range from 20° to 60° C. and the concentration of alkali metal hydroxide having to be kept above 35% by weight, based on the aqueous phase, throughout the reaction. However, the products contain up to 25% by weight of unreacted starting product and are unacceptable from the point of view of color.

Accordingly, the problem addressed by the present invention was to provide an improved process for the production of end-capped nonionic surfactants of the methyl mixed ether type which would be distinguished by a reduced content of unreacted starting material and by improved color quality.

DESCRIPTION OF THE INVENTION

The present invention relates to a process for the production of end-capped nonionic surfactants corresponding to formula (I):

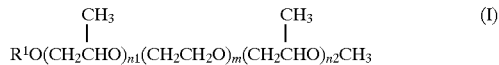

in which $R^1$ is an alkyl and/or alkenyl group containing 6 to 22 carbon atoms, n1 and n2 independently of one another stand for 0 or for numbers of 1 to 10 and m stands for numbers of 1 to 20, by reaction of alcohol alkoxylates with dialkyl sulfates, in which (a) fatty alcohol polyglycol ethers corresponding to formula (II):

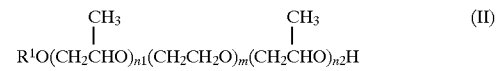

in which $R^1$, n1, n2 and m are as defined above, are reacted with solid substantially water-free bases (III), (b) the alcoholates formed are etherified with dialkyl sulfates (IV), (c) water is added to the crude ethers in such a quantity that phase separation occurs and (d) the organic valuable phases are removed by methods known per se.

A process in which alcoholate formation and etherification are carried out in the presence of aqueous bases is already known from the prior art. However, it has surprisingly been found to be of far greater advantage to carry out alcoholate formation and etherification in two stages and to use solid substantially water-free bases as reactants because products with a relatively low content of unreacted starting material can be obtained. In addition, the use of borohydrides in the alcoholate formation step leads to products with considerably improved color quality.

Fatty alcohol polyglycol ethers

Fatty alcohol polyglycol ethers are known nonionic surfactants which may be obtained by the relevant methods of preparative organic chemistry, for example by the addition of alkylene oxides to fatty alcohols. Depending on the alkoxylation catalyst, the ethers may have a conventional broad homolog distribution or a narrow homolog distribution.

Typical examples of fatty alcohol polyglycol ethers which may be used as starting materials in accordance with the invention are products of the addition of 5 to 15 moles of ethylene oxide and optionally 1 mole of propylene oxide to caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols.

Particularly preferred starting materials are fatty alcohol polyglycol ethers corresponding to formula (II) in which $R^1$ is an alkyl group containing 12 to 18 carbon atoms, n1 stands for 0, m stands for numbers of 5 to 15 and n2 stands for the number 1 or in which $R^1$ is an alkyl group containing 6 to 10 carbon atoms, n1 stands for the number 1, m stands for numbers of 5 to 15 and n2 has a value of 0.

Bases

Suitable bases are primarily the oxides, hydroxides and carbonates of the alkali and/or alkaline earth metals. Typical examples are lithium hydroxide, sodium carbonate, sodium hydrogen carbonate, magnesium oxide, magnesium hydroxide, calcium oxide and calcium hydroxide. It is preferred to use sodium hydroxide and/or potassium hydroxide, preferably potassium hydroxide. The bases are used in the form of solid products, i.e. for example beads, flakes or pellets, and generally have a water content from their production of less than 15% by weight and, more particularly, less than 10% by weight. A water content of this order is tolerable in the process according to the invention although, basically, water-free products (which unfortunately are not readily available on an industrial scale) would be preferred.

It has been found to be of advantage to use the fatty alcohol polyglycol ethers (II) and the bases (III) in a molar ratio of 1:1.0 to 1:1.5 and preferably in a molar ratio of 1:1.1 to 1:1.4.

Alcoholate formation

The step in which the alcoholate is formed is normally carried out at a temperature of 20° to 98° C. and preferably at a temperature of 40° to 80° C. In one preferred embodiment of the invention, alkali metal and/or alkaline earth metal borohydrides are added to the fatty alcohol polyglycol ethers, which leads to substantially colorless products. Typical examples of suitable borohydrides are potassium borohydride, magnesium borohydride and, in particular, sodium borohydride. Other suitable stabilizers are lithium alanate and hypophosphorous acid and alkali metal salts thereof which may even be used in combination with sodium borohydride. The borohydrides are normally used in quantities of 100 to 1000 ppm and, more particularly, in quantities of 300 to 700 ppm, based on the fatty alcohol polyglycol ethers.

Dialkyl sulfates

In the context of the invention, dialkyl sulfates are understood to be diethyl sulfate and, in particular, dimethyl sulfate. Basically, mixtures of dimethyl and diethyl sulfate and higher alkyl sulfates (providing they are available in commercial quantities) may also be used as alkylating agents for the process according to the invention. The fatty alcohol polyglycol ethers (II) and the dialkyl sulfates (IV) are preferably used in a molar ratio of 1:1.0 to 1:1.5 and, more particularly, in a molar ratio of 1:1.1 to 1:1.4.

Etherification

The etherification step is advantageously carried out at a lower temperature than the alcoholate formation. A temperature in the range from 20° to 100° C. and, more particularly, in the range from 40° to 50° C. has proved to be optimal.

Phase separation and aftertreatment

The aftertreatment of the crude alkylation products with water has two objectives. Firstly, the quantity of inorganic salt formed during the etherification step migrates into the water phase and, secondly, unreacted dialkyl sulfate is decomposed. To this end, it has proved to be of advantage to carry out the phase separation at a temperature of 70° to 98° C. After phase separation, the ether is normally dried and unreacted base is filtered off. If necessary, the content of free alkylating agent can be further reduced by adding 0.1 to 1% by weight of an amino compound, for example ammonia, glycine or an alkanolamine, to the ether, if desired even before phase separation.

Commercial Applications

The end-capped nonionic surfactants obtainable by the process according to the invention are distinguished by excellent wetting power, are extremely low-foaming and are capable in particular of defoaming formulations containing anionic surfactants. Accordingly, they are particularly suitable for the production of machine bottle washing detergents in which they may be present in quantities of 1 to 50% by weight and preferably in quantities of 5 to 35% by weight, based on the detergent.

The following Examples are intended to illustrate the invention without limiting it in any way.

EXAMPLES

Examples 1 to 4

500 g of $C_{12/14}$ cocoalcohol+6 EO and 500 ppm of sodium borohydride, based on the polyglycol ether, were introduced into a three-necked flask equipped with a dropping funnel, stirrer and reflux condenser and alkali metal hydroxide flakes were added in portions with intensive stirring over a period of 2 hours at a temperature of 80° C. The alcoholate mixture was then cooled to 45° C. and, after the addition of dimethyl sulfate, was stirred first for 1 hour at 45° C., then for 2 hours at 50° C. and, finally, for 1 hour at 60° C. 500 g of water were then added, the mixture was heated to 80°–85° C. and was stirred for another 2 hours during which separation occurred. The sulfate salt formed being dissolved almost completely in the aqueous phase. After phase separation, the organic useful-material phase was dried in vacuo and then filtered. Particulars of the quantity ratios used and the characteristic data of the products can be found in Table 1 where the percentages shown are percentages by weight.

Example 5

Example 1 was repeated using octanol+1 PO+10 EO. The results are set out in Table 1.

Example 6

Example 1 was repeated using $C_{12/14}$ cocofatty alcohol+ 10 EO+1 PO. The results are set out in Table 1.

Comparison Example C1

Example 1 was repeated except that no sodium borohydride was added in the alcoholate formation step. The results are set out in Table 1.

Comparison Example C2

Example 1 was repeated using a corresponding quantity of 50% by weight potassium hydroxide solution instead of the KOH flakes and leaving out the sodium borohydride. The results are set out in Table 1.

TABLE 1

| | Etherification with Dimethyl Sulfate | | | | |
|---|---|---|---|---|---|
| Ex. | Base | F:Base | F:DMS | Yield % of Th. | Salt % | Color Gard. |
| 1 | KOH | 1:1.27 | 1:1.15 | 95 | <1 | <1 |
| 2 | KOH | 1:1.30 | 1:1.20 | 95 | <1 | <1 |
| 3 | KOH | 1:1.40 | 1:1.30 | 94 | <1 | <1 |
| 4 | NaOH | 1:1.30 | 1:1.20 | 93 | <1 | <1 |
| 5 | KOH | 1:1.27 | 1:1.15 | 95 | <1 | <1 |
| 6 | KOH | 1:1.27 | 1:1.15 | 91 | <1 | <1 |
| C1 | KOH | 1:1.27 | 1:1.15 | 95 | <1 | 11 |
| C2 | KOH | 1:1.27 | 1:1.15 | 76 | <1 | Red |

Legend:
F:base = Molar ratio of fatty alcohol polyglycol ether to base
F:DMS = Molar ratio of fatty alcohol polyglycol ether to dimethyl sulfate TABLE 1-continued Etherification with Dimethyl Sulfate

| Ex. | Base | F:Base | F:DMS | Yield % of Th. | Salt % | Color Gard. |
|---|---|---|---|---|---|---|

Salt = Content of inorganic sulfate in the product
Color = Gardner color number

We claim:

1. A process for the production of end-capped nonionic surfactants corresponding to formula (I):

$$R^1O(CH_2CHO)_{n1}(CH_2CH_2O)_m(CH_2CHO)_{n2}CH_3 \quad\quad \overset{CH_3}{|} \quad\quad \overset{CH_3}{|} \quad\quad (I)$$

in which $R^1$ is an alkyl or alkenyl group containing 6 to 22 carbon atoms, n1 and n2 independently of one another are 0 or a number of from 1 to 10, and m is a number of from 1 to 20, comprising the steps of A) reacting at least one fatty alcohol polyglycol ether corresponding to formula (II):

$$R^1O(CH_2CHO)_{n1}(CH_2CH_2O)_m(CH_2CHO)_{n2}H \quad\quad \overset{CH_3}{|} \quad\quad \overset{CH_3}{|} \quad\quad (II)$$

in which $R^1$, n1, n2 and m are as defined above, with a solid base (III), having a water content of less than 15% by weight, in the presence of an alkali metal borohydride, an alkaline earth metal borohydride, or both;

B) etherifying the resulting alcoholate or alcoholates with dimethyl sulfate,

C) adding water to the etherified alcoholate or alcoholates in an amount sufficient to result in phase separation into an organic phase and an aqueous phase; and D) separating the organic phase from the aqueous phase.

2. The process of claim 1 wherein in formula II, $R^1$ is an alkyl group containing from 12 to 18 carbon atoms, n1 is 0, m is a number of from 5 to 15, and n2 is 1.

3. The process of claim 1 wherein in formula II, $R^1$ is an alkyl group containing 6 to 10 carbon atoms, n1 is 1, m is a number of from 5 to 15, and n2 is 0.

4. The process of claim 1 wherein in step A) the solid base is sodium hydroxide, potassium hydroxide, or both.

5. The process of claim 1 wherein the ether of formula II and the solid base (III) are present in a molar ratio of from about 1:1 to about 1:1.5.

6. The process of claim 1 wherein step A) is carried out at a temperature in the range of from about 20° to about 98° C.

7. The process of claim 1 wherein in step B) the alcoholate or alcoholates and the dimethyl sulfate are present in a molar ratio of from about 1:1 to about 1:1.5.

8. The process of claim 1 wherein step B) is carried out at a temperature in the range of from about 20° to about 100° C.

9. The process of claim 1 wherein step C) is carried out at a temperature in the range of from about 70° to about 98° C.

10. The process of claim 1 wherein in step A) the solid base is an oxide, hydroxide, or carbonate of an alkali or alkaline earth metal.

11. The process of claim 1 wherein in step A) the solid base has a water content of less than 10% by weight.

12. The process of claim 5 wherein said molar ratio is from about 1:1.1 to about 1:1.4.

13. The process of claim 1 wherein in step A) the borohydride is sodium borohydride, potassium borohydride, or magnesium borohydride.

14. The process of claim 1 wherein the borohydride is present in from about 100 to about 1000 ppm. based on the at least one ether of formula II.

15. The process of claim 14 wherein the borohydride is present in from about 300 to about 700 ppm.

16. The process of claim 6 wherein said temperature is in the range of from about 40° to about 80° C.

17. The process of claim 8 wherein said temperature is in the range of from about 40° to about 50° C.

18. The process of claim 1 wherein in step A) the solid base is sodium hydroxide, potassium hydroxide, or both; the ether of formula II and the solid base (III) are present in a molar ratio of from about 1:1 to about 1:1.5; the borohydride is present in from about 0.1 to about 1% by weight, based on the at least one fatty alcohol polyglycol ether; step A) is carried out at a temperature in the range of from about 20° to about 98° C.; in step B) the alcoholate or alcoholates and the dimethyl sulfate are present in a molar ratio of from about 1:1 to about 1:1.5; step B) is carried out at a temperature in the range of from about 20° to about 100° C.; and step C) is carried out at a temperature in the range of from about 70° to about 98° C.

19. The process of claim 18 wherein in formula II, $R^1$ is an alkyl group containing from 12 to 18 carbon atoms, n1 is 0, m is a number of from 5 to 15, and n2 is 1, or wherein in formula II, $R^1$ is an alkyl group containing 6 to 10 carbon atoms, n1 is 1, m is a number of from 5 to 15, and n2 is 0.

20. The process of claim 18 wherein in step A) the solid base is sodium hydroxide, potassium hydroxide, or both; the borohydride is sodium borohydride, potassium borohydride, or magnesium borohydride, and the borohydride is present in from 100 to 1000 ppm, based on the at least one ether of formula II.

* * * * *